United States Patent
Staebler et al.

Patent Number: 5,254,312
Date of Patent: Oct. 19, 1993

[54] APPARATUS FOR COLLECTING A BLOOD SAMPLE FROM A SEALED TUBE

[76] Inventors: Charles R. Staebler, 7874 Van Raden, Pinckney, Mich. 48169; Rodney D. Capps, II, 1274 Shevchenko, Ann Arbor, Mich. 48103; John F. Richards, 3849 Van Amberg Rd., Brighton, Mich. 48116

[21] Appl. No.: 884,132

[22] Filed: May 18, 1992

[51] Int. Cl.⁵ .............................................. B01L 3/02
[52] U.S. Cl. .................................... 422/100; 422/102; 422/103; 73/863.85; 73/864.74; 128/764; 128/765; 128/767; 128/768; 604/411; 604/414
[58] Field of Search .............. 422/99, 100, 102, 103; 604/411, 412, 413, 414; 128/763–765, 767, 768; 73/863.85, 864.74; 30/124, 366

[56] References Cited

U.S. PATENT DOCUMENTS

| | | | |
|---|---|---|---|
| 3,713,780 | 1/1973 | Shapiro | 23/259 |
| 4,080,965 | 3/1978 | Phillips | 128/214 D |
| 4,116,066 | 9/1978 | Mehl et al. | 604/414 X |
| 4,176,451 | 12/1979 | McMorrow | 422/99 X |
| 4,314,570 | 2/1982 | Sarstedt | 422/102 X |
| 4,397,725 | 8/1983 | Enzer et al. | 422/61 X |
| 4,399,103 | 8/1983 | Ferrara | 436/180 X |
| 4,927,605 | 5/1990 | Dorn et al. | 128/763 X |
| 5,070,884 | 12/1991 | Columbus et al. | 128/763 X |
| 5,154,188 | 10/1992 | Ebert | 422/102 X |
| 5,163,583 | 11/1992 | Whitworth | 604/411 X |

FOREIGN PATENT DOCUMENTS 0350792   1/1990   European Pat. Off. .

*Primary Examiner*—Jill A. Johnston
*Assistant Examiner*—Maureen M. Wallenhorst
*Attorney, Agent, or Firm*—Harness, Dickey & Pierce

[57] ABSTRACT

An apparatus for obtaining a blood sample in a test tube from a sealed container. The apparatus includes a main body having a cup-like portion with side walls and a bottom portion cooperating to define a central cavity for receiving the sealed container. The main body also includes provisions which enable mounting to the test tube so that the cup-like portion extends into the test tube. A piercing element is positioned within the cavity and has a tip capable of penetrating the sealed container when the container is inserted into the cavity so that an opening is formed in the container through which the blood sample can be obtained in the test tube.

4 Claims, 3 Drawing Sheets

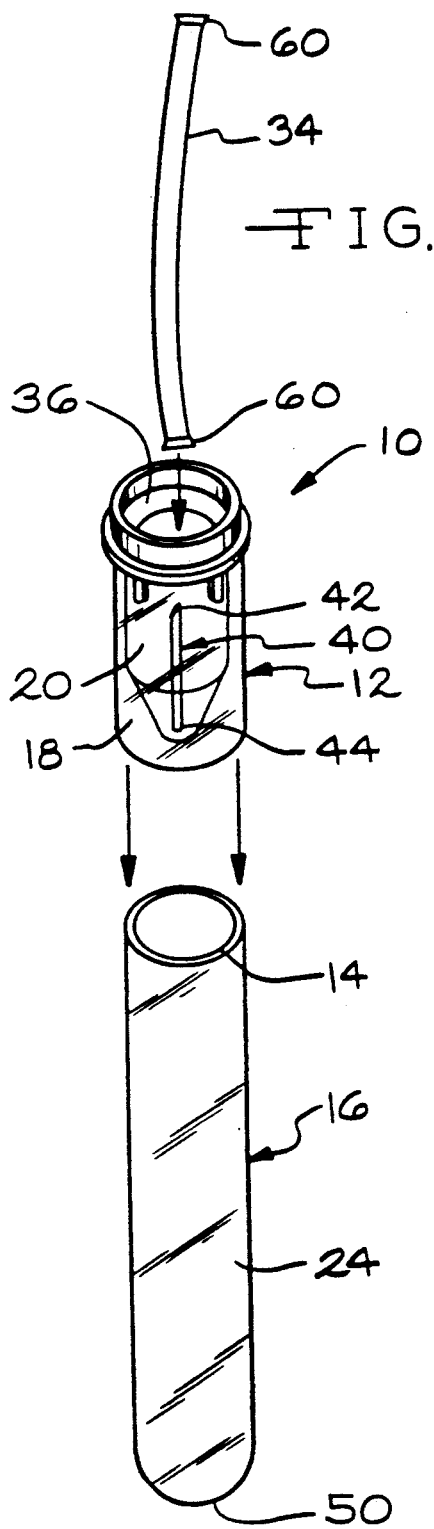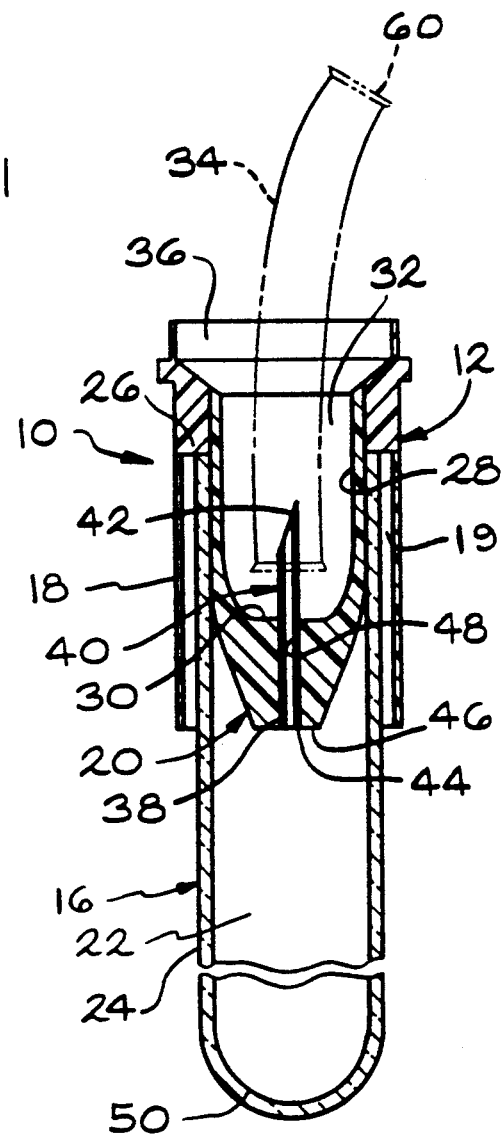
FIG. 1
FIG. 2

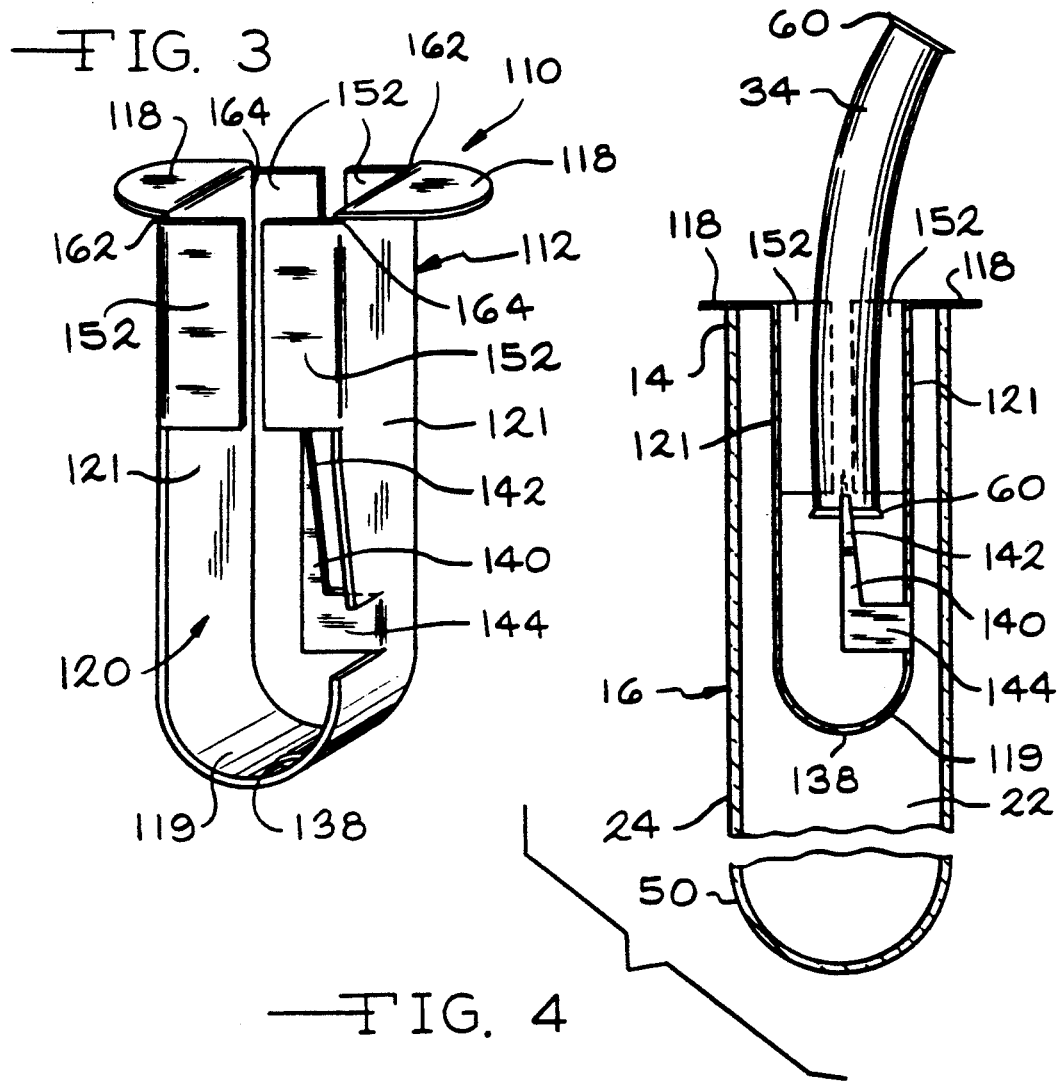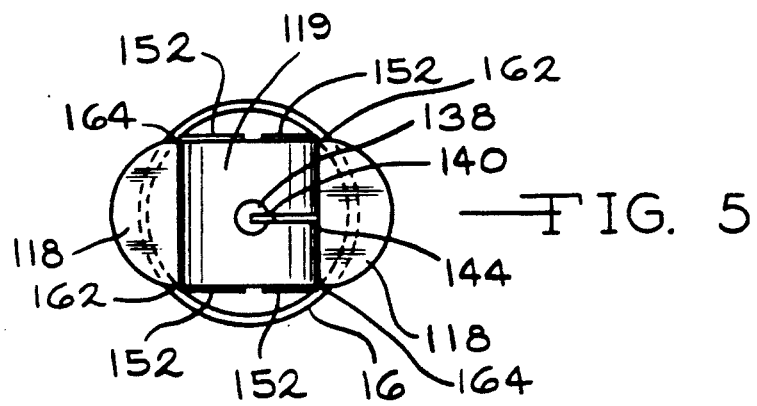

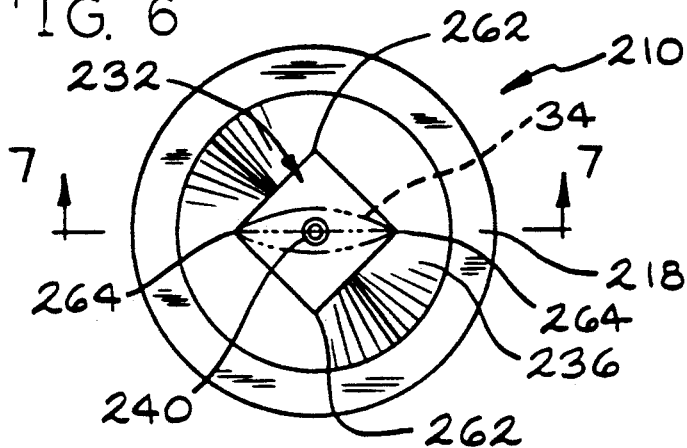
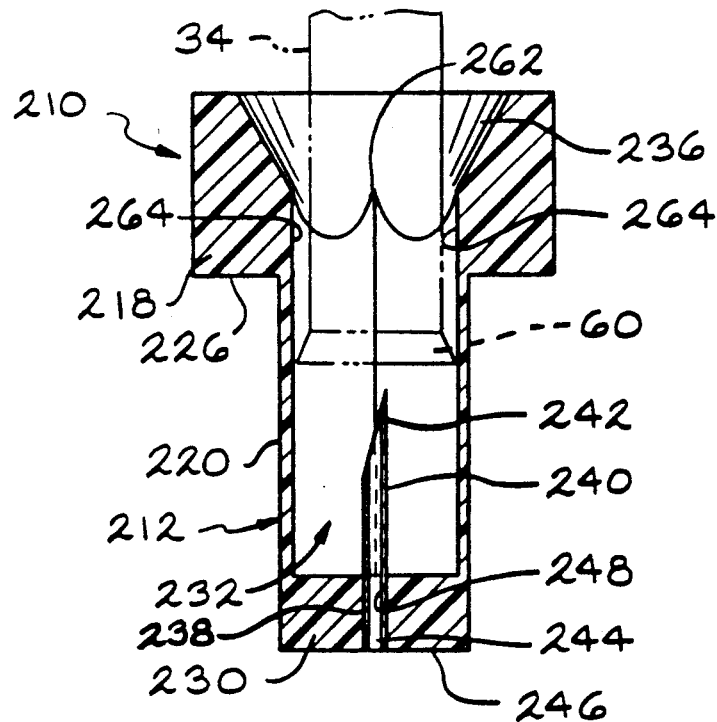

APPARATUS FOR COLLECTING A BLOOD SAMPLE FROM A SEALED TUBE

BACKGROUND AND SUMMARY OF THE INVENTION

This invention generally relates to the handling of blood samples and more specifically to the collecting of a blood sample from a sealed container having blood disposed therein.

Over the last century, the medical community has become aware of the desire to guard against the transmission of fluid-borne infections to those patients which are most vulnerable. Particularly susceptible patients include those having open wounds or undergoing surgical procedures. As a result of this concern for the patient, various methods and techniques have been developed to inhibit the transmission of common infectants. These prior methods and techniques include, but are not limited to, the development of a sterile operating environment and the employment of various barrier-type equipment including masks, gowns, gloves, etc. Unfortunately, the procedures have been primarily directed to prohibiting the transmission of infectants and other agents to the patient. There is now an equal concern with protecting the doctor, nurse, lab technician and others against the transmission of infection from the patient.

Since the early 1980's, concern has existed in the medical community regarding the potential transmission of blood-borne pathogens such as the hepatitis B virus (HBV), the human T cell lymphotropic viruses (HTLV), the human immunodeficiency viruses (HIV), and a number of other infectants during the performance of medical procedures. Any medical procedure which involves the handling of blood and/or other body fluids carries with it the potential for the transmission of the above-mentioned infectants. To protect against infection, barrier-type equipment of the above discussed variety has been utilized. This equipment, however, does not always lend itself to use in the laboratory environment where it may prove to be prohibitorily cumbersome during the performance of some tasks.

It is therefore an object of this invention to provide for an apparatus and method which may be used to reduce the exposure risk during the collection and handling of blood and other body fluids during laboratory procedures. In particular, it is believed that the apparatus and method of the present invention will find particular utility with work performed at blood banks and blood donation centers. As it will be seen from the discussion more fully set out below, the invention has general utility to any situation which requires the taking of a body fluid sample from a tube-like container having the body fluid sample disposed therein. It should be noted that neither the present invention nor any other device can unequivocally warrant to be a completely effective containment or barrier against fluid-borne infectants. Rather, usage of the present invention will allow certain steps in current practice to be circumvented, thereby lowering, but not eliminating the risk of exposure and infection.

SUMMARY OF THE INVENTION

Blood donation has become a common experience. Both the basic procedure and the value of this service are well understood and accepted by the public. Therefore, no specific elaboration on these points is necessary and the following discussion is confined to a small portion of the equipment that is typically used during the procedure.

Blood is drawn from a donor by inserting a needle into an area, typically the forearm, where veins are present. The basic equipment used when drawing blood includes an integral system having a needle, a length of tubing and a collection bag. The tubing is typically 30 to 40 inches in length and transfers the drawn blood from the needle into the collection bag. An anti-coagulant coats the interior of this system to prevent clotting of the blood during its withdrawal from the donor and subsequent storage. Collection of one full bag of blood represents a volume of approximately 500 cc., or one pint, and is generally known as a "unit of blood".

Prior to the withdrawal of the needle from the donor's arm, clamps are applied on the tubing adjacent to both the needle and the collection bag. This procedure retains blood throughout the length of the tubing. After the needle has been withdrawn from the donor's arm and separated from the tubing, the tubing is heat sealed along its length, transversely thereto, at approximately 3 inch intervals to form sealed "segments" or vials containing a representative sampling of the blood disposed in the collection bag. The segments are stored intact with the unit of blood and are available, without disturbing the contents of the collection bag, for testing. Typically, the tests involve blood grouping and screening for various factors that might result in the acceptance or rejection of the unit of blood for use, either completely or with respect to a particular patient.

At the time when such testing is to be performed, a segment is separated from the tubing. Previously, after being separated, one end of the segment was cut with scissors and a few drops of the blood sample was dispensed from the segment into a test tube for analysis. Although the technicians performing these tasks are highly skilled, incidents do occur where blood is uncontrollably expelled from the segment into the laboratory environment. "Squirting" of the blood can result from localized pressure on the segment during the cutting of the segment and from a failure to accurately insert the opened end of the segment into the test tube. The result is that the technician and various areas of the laboratory may become contaminated with the untested blood. Additionally, final disposal of the segment results in an opened container from which the remaining amount of the blood sample could be easily released into the environment.

The present invention seeks to greatly reduce the occurrences of the above noted spillages. In accomplishing this, the apparatus of the present invention provides for a cup or cup-like portion which is placed upon the open end of the test tube and extends partially into the receptacle portion of the test tube. Once the cup has been positioned on the test tube, the segment is slid into the cup and becomes impaled upon and penetrated by a piercing element which is mounted to the innermost portion of the cup. Under the influence of gravity or by exerting mild pressure on the segment, a sample of blood may be expelled from the segment through the opening created by the piercing element into the test tube without substantial risk of contaminating areas outside of the test tube with the blood. It is intended that the segment will remain in the guide and that both the segment and the guide will be discarded together. Subsequent expulsion of blood from the segment through the opening during disposal is reduced because of the near capillary size of the opening formed by the piercing element.

As seen from the above discussion outlining the present invention, a method for obtaining a blood sample in a receptacle from a hermetically sealed container having blood contained therein includes the steps of: inserting at least a portion of the hermetically sealed container into the receptacle; and piercing the inserted portion of the hermetically sealed container to create an opening from which blood can flow into the receptacle.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 1 is an unassembled perspective view of an apparatus of the present invention;

FIG. 2 is a sectional view taken longitudinally through the embodiment shown in FIG. 1 after assembly;

FIG. 3 is a perspective view of a second embodiment of an apparatus embodying the principles of the present invention;

FIG. 4 is a longitudinal sectional view of the embodiment illustrated in FIG. 3 mounted on a test tube;

FIG. 5 is a plan view of the embodiment of FIG. 3 mounted on a test tube;

FIG. 6 is a plan view of a third embodiment of an apparatus incorporating the principles of the present invention; and FIG. 7 is a longitudinal sectional view taken substantially along line 7—7 in FIG. 6 showing the internal structure of the embodiment.

DETAILED DESCRIPTION OF THE PREFERRED EMBODIMENTS

Referring now to the drawings, three specific embodiments of an apparatus for collecting a blood sample from a sealed container or segment, as discussed above, are shown. Each specific embodiment provides reliability in reducing the incidents where blood is potentially spilled resulting in contamination of the laboratory area and various laboratory instruments.

In general, an apparatus incorporating the principles of the present invention includes a cup or cup-like portion which is capable of being mounted onto the open end of a test tube so that it extends into the cavity of the test tube generally toward the closed end of the test tube. In addition to the cup, the apparatus includes a mounting portion that may be dimensioned for a specific test tube size, such as a 10 cc. test tube. Similarly, the cup is dimensioned to fit within the cavity and the side wall of the specific test tube size.

The cup further defines a receiving cavity for receiving the segment in which the sample of blood is disposed. Positioned centrally within the receiving cavity is a sharp knife-like or needle-like piercing element or implement. The implement is aligned so as to extend upward from the bottom of the cup generally along a central longitudinal axis of the apparatus and the test tube.

As the segment is inserted into the receiving cavity, the segment becomes impaled upon and penetrated by the implement forming an opening in the segment 34. Under the forces of gravity, or by applying slight pressure to the segment, the sample of blood is expelled through the opening in the segment 34. A passageway is provided in the lowermost portion of the cup to allow the blood sample to flow out of the apparatus and into the cavity of the test tube without any significant risk of the blood sample being spilled.

With the general principles of the apparatus having been outlined above, the three specific embodiments of the invention will now be discussed in further detail.

A first embodiment of the apparatus incorporating the principles of the present invention is generally shown in FIGS. 1 and 2 and is designated at 10. As seen in FIG. 1, the apparatus 10 generally includes a body 12, made of acrylic, styrene or a similar material that is non-reactive with blood, which is sized so as to enable fitting onto the open end 14 of a test tube 16. It is preferred that the apparatus 10 is specifically dimensioned for a particular size of test tube 16, such as a standard 10 cc. test tube. Obviously, the apparatus 10 could be dimensioned for other sizes of test tubes as well.

The body 12 further includes a cylindrical skirt 18 which is outwardly radially spaced from and concentric with a cup portion 20 (hereinafter cup 20). The skirt 18 and cup 20 are integrally formed and dimensioned so that the skirt 18 slides over the exterior of the test tube 16 and the cup 20 slides into the test tube 16. When mounted to the test tube 16, the dimensions of the cup 20 allow for the cup 20 to extend into a cavity 22 defined by the side wall 24 of the test tube. The skirt 18 is dimensioned to fit over the exterior of the side wall 24 with the side wall 24 positioned in gap 19 between the skirt 18 and the cup 20. A shoulder 26 limits the depth with which the body 12 is received onto the test tube 16.

The cup 20 generally includes a side wall 28 and a bottom wall 30 which cooperate to define receiving cavity 32 into which a sealed container or segment 34 is received. The upper end of the receiving cavity 32 is defined by a tapered mouth 36 that aids in directing the segment 34 into the receiving cavity 32.

As mentioned above, the segment 34 is an elongated hollow plastic or rubber tube that is heat or otherwise sealed at its ends to retain a quantity of blood therein. In forming the segments 34, the tube, which extends from the needle to the collection bag, is heat sealed at intervals along its length thereby producing a number of the segments 34. As a result of this heat sealing, rigid flanges 60 are formed on the respective ends of the segment 34.

A passageway 38 is defined through the bottom wall 30 of the cup 20 and allows for communication between the receiving cavity 32 of the apparatus 10 and the cavity 22 of the test tube 16 for reasons which will readily become apparent. Positioned within the passageway 38 is a metal cannula 40 whose upper end 42 has been ground into a sharp beveled point. Preferably stainless steel is used for the cannula 40. The cannula 40 is press fit or otherwise embedded into the passageway 38 and an adhesive or epoxy is used to secure the cannula 40 to the cup 20 stabilizing the sharp upper end 42 of the cannula 40.

The length of the cannula 40 is provided so that the sharp upper end 42 is positioned within the receiving cavity 32 and recessed from the mouth 36. This positioning minimizes the risk that a technician using the apparatus 10 will accidentally puncture his/her finger. The opposing or stub end 44 of the cannula is mounted flush with the bottom surface 46 of the cup 20 to allow the apparatus 10 to stand upright when not being used.

The cannula 40 is further mounted so as to be generally aligned with the longitudinal axis of the cup 20 and the test tube 16. In use, when a segment 34 is inserted into the receiving cavity 32 of the body 12, the segment 34 is pierced by the sharp upper end 42 and becomes impaled upon the cannula 40. When the upper end 42 of the cannula 40 is positioned interiorly of the segment 34, the blood sample can pass through a lumen 48 in the cannula 40 into the cavity 22 of the test tube 16. The expelling of the blood sample into the test tube 16 occurs under the force of gravity or by the application of a slight external pressure to the segment 34. By terminating the stub end 44 of the cannula 40 as discussed above, the drops of the blood sample easily break free of the apparatus 10, falling to the closed end 50 of the test tube 16, without any significant creep back onto the bottom surface 46 of the cup 20.

A second embodiment of the present invention is generally illustrated in FIGS. 3, 4 and 5. In this particular embodiment, an apparatus 110 for collecting a blood sample is constructed from a metal stamping which is bent into the shown configuration. Preferably stainless steel is used as the metal for the stamping.

The apparatus 110 generally includes a body 112 which is configured to be mounted onto the open end 14 of a test tube 16. The body 112 is integrally formed and includes a cup-shaped portion 120 configured to extend into the cavity 22 defined by the side wall 24 of the test tube 16. The cup-shaped portion 120 is generally a U-shaped member having a pair of flanges or ears 118 extending transversely off of the upper ends of a pair of opposing side walls 121. The side walls 121 are joined together at their lowermost end by a curved end wall 119.

A piercing element or implement 140 is integrally formed from one of the side walls 121 and is bent so as to be oriented between the opposing side walls 121. Additionally, the implement 140 generally aligned with the longitudinal axis of the test tube 16 and the apparatus 110. The lower end 144 of the implement 140 attaches the implement 140 to the side wall 121 and the upper end 142 of the implement 140 is tapered into a sharp point. An aperture 138 is formed in the end wall 119 of the cup 120 and is axially aligned with the implement 140 for reasons which will become apparent.

To protect the sharp upper end 142 of the implement 140, the apparatus 110 is provided with shield walls 152. Two shield walls 152 are integrally formed with each side wall 121 and extend transversely from the upper ends thereof toward the opposing side wall 121 giving the upper end of the cup 120 a square or box-like construction. The shield walls 152 extend down along the side walls 121 a distance which positions the sharp upper end 142 of the implement 140 between the shield walls 152. In this manner, the shield walls 152 protect a technician from becoming inadvertently pricked by the sharp upper end 142 of the implement 140 during routine handling of the apparatus 110. Additionally, the implement 140 itself is protected from damage during handling or storage.

When being used, the cup 120 of the apparatus 110 extends internally of the test tube cavity 22. As such, the dimensions of the cup 120 may be provided to enable use with a specific size of test tube 16. The transversely oriented flanges 118 enable the apparatus 110 to rest on the open end 14 of the test tube 16 suspending the cup 120 above the closed end 50 of the test tube 16. When a segment 34 is inserted into the receiving space defined between the opposing side walls 121 of the cup 120, the segment 34 is pierced by the sharp upper end 142 of the implement 140 and becomes impaled upon the implement 140. The resulting incision formed in the segment 34 and permits a drop of the blood sample contained on the segment 34 to travel down the implement 140 where it is passed through the aperture 138 onto the closed end 50 of the test tube 16.

The distance between opposed corners 162 and 164 of the square configuration formed by the side walls 121 and the shield walls 152 can be dimensioned so as to correspond with the width of the rigid flange 60 of the segment 34. Because of this, as the segment 34 is inserted into the body 112, the flange 60 will be oriented between one set of the opposing corners 162 or 164 ensuring that the body of the segment 34 is aligned to be pierced by the implement 140. The need for a lab technician to manually guide the segment 34 onto the implement 140 is therefore eliminated.

The third and preferred embodiment of the present invention is shown in FIGS. 6 and 7. An apparatus 210 is illustrated in FIGS. 6 and 7 which utilizes the end flanges 60 to guide and ensure impaling of the segment 34 upon a cannula 240 mounted in the apparatus 210.

The apparatus 210 includes a body 212, of acrylic or similar material, having a cup 220 which is shaped to fit within the interior cavity 22 of a test tube 16. As in the prior embodiments, the cup 220 may have dimensions which dictate use with a specific size of test tube 16. Integrally formed with the upper end of the cup 220 is a radially extending flange 218. The flange 218 includes a shoulder 226 which limits the distance that the cup 220 can be inserted into the test tube 16. A receiving cavity 232 is formed centrally in the cup 220. The receiving cavity 232 itself has a square transverse sectional shape and merges with a tapered or conical mouth 236 at its upper end.

The cannula 240, preferably made of stainless steel, is press-fit or adhesively secured within a passageway 238 centrally formed in a bottom wall 230 of the cup 220. The cannula 240 is aligned so as to generally correspond with the longitudinal axis of the test tube 16 and the apparatus 210. In a manne similar to the first embodiment, the upper end 242 of the cannula 240 is shaped into a sharp beveled point. The length of the cannula 240 is provided so that the sharp upper end 242 is sufficiently recessed from the mouth 236 to minimize the risk of the upper end 236 becoming damaged during handling and to minimize the risk of a laboratory technician accidentally puncturing his/her finger. The stub end 244 of the cannula 240 is mounted flush with a lowermost surface 246 of the bottom wall 230.

The distance between opposed corners 262 and 264 of the receiving cavity 232 are dimensioned so as to correspond with the width of the rigid flange 60 of the segment 34. Because of this, as the segment 34 is inserted into the receiving cavity 232 during use of the apparatus 210, the flange 60 will be oriented with a pair of the opposed corners 262 or 264 thereby ensuring alignment of the segment 34 substantially directly over the cannula 240. As the segment 34 is inserted into the receiving cavity 232, the segment 34 is directed so as to be penetrated by the upper end 242 of the cannula 240 and impaled thereupon. The square sectional shape of the receiving cavity 232 eliminates any need for a lab technician to manually direct the segment 34 to ensure piercing by the cannula 240.

As in the previous embodiments, once the segment 34 has been penetrated, the blood sample is expelled from the segment 34 through a lumen 248 in the cannula 240 and deposited within the cavity 22 of the test tube 16.

While the above description constitutes the preferred embodiments of the present invention, it will be appreciated that the invention is susceptible to modification, variation and change without departing from the proper scope and fair meaning of the accompanying claims.

What is claimed is:

1. An integrally formed apparatus for use with a receptacle in obtaining a blood sample from a sealed container, said apparatus comprising:

a body including an upper end, a lower end, and side walls disposed between said upper and lower ends, said side walls being spaced apart and cooperating to generally define a central cavity in said body for receiving said sealed container therein, said side walls being opposingly positioned to one another and connected together by said lower end thereby providing said body with a substantially U-shape having open sides adjacent to said side walls;

means formed on said body for mounting said body to said receptacle such that said body extends into said receptacle; and an element integrally formed from a portion of said body and being located within said central cavity and having a sharp tip directed toward said upper end of said body, said element being capable of penetrating said sealed container when said sealed container is received within said central cavity thereby providing an opening in said sealed container through which said blood sample can flow into said receptacle when said body is mounted on said receptacle.

2. An apparatus for use with a receptacle in obtaining a blood sample according to claim 1 wherein said side walls of said body include means extending from said side walls for shielding said slitting element from damage.

3. An apparatus for use with a receptacle in obtaining a blood sample according to claim 2 wherein said shielding means includes a tab extending transversely from at least one of said side walls toward the opposing one of said side walls, said tab being located at a position generally corresponding to said sharp tip and shielding said sharp tip.

4. An integrally formed apparatus for use with a receptacle in obtaining a blood sample from a sealed container, said apparatus comprising:

a body including an upper end, a lower end, and side walls disposed between said upper and lower ends, said side walls being spaced apart and cooperating to generally define a central cavity in said body for receiving said sealed container therein;

means formed on said body for mounting said body to said receptacle such that said body extends into said receptacle; and and element integrally formed from a portion of said body and being located within said central cavity and having a sharp tip directed toward said upper end of said body, said element formed by a portion of one of said side walls being folded into said central cavity, said element being capable of penetrating said sealed container when said sealed container is received within said central cavity thereby providing an opening in said sealed container through which said blood sample can flow into said receptacle when said body is mounted on said receptacle.

* * * * *